(12) United States Patent
Llorente Alonso et al.

(10) Patent No.: US 10,786,590 B2
(45) Date of Patent: Sep. 29, 2020

(54) VOLATILE SUBSTANCE-EVAPORATOR DEVICE

(71) Applicant: ZOBELE ESPAÑA, S.A., Barcelona (ES)

(72) Inventors: Joaquim Llorente Alonso, Barcelona (ES); Fernando Mayor Sans, Barcelona (ES); Julio Cesar Ruiz Ballesteros, Barcelona (ES)

(73) Assignee: ZOBELE ESPAÑA, S.A., Barcelona (ES)

( * ) Notice: Subject to any disclaimer, the term of this patent is extended or adjusted under 35 U.S.C. 154(b) by 0 days.

(21) Appl. No.: 15/325,529

(22) PCT Filed: Jul. 10, 2015

(86) PCT No.: PCT/ES2015/070543
§ 371 (c)(1),
(2) Date: Jan. 11, 2017

(87) PCT Pub. No.: WO2016/005648
PCT Pub. Date: Jan. 14, 2016

(65) Prior Publication Data
US 2017/0143863 A1    May 25, 2017

(30) Foreign Application Priority Data
Jul. 11, 2014 (ES) .................................. 201431049

(51) Int. Cl.
*A61L 9/03* (2006.01)
*A61L 9/02* (2006.01)

(52) U.S. Cl.
CPC .................. *A61L 9/03* (2013.01); *A61L 9/02* (2013.01); *A61L 2209/133* (2013.01)

(58) Field of Classification Search
CPC ......... A61L 9/03; A61L 2209/133; A61L 9/02
(Continued)

(56) References Cited

U.S. PATENT DOCUMENTS 4,781,895 A    11/1988 Spector
6,144,801 A    11/2000 Lehoux et al.
(Continued)

FOREIGN PATENT DOCUMENTS

ES    2199863 T3    3/2004
FR    2760194 A1    9/1998
(Continued)

OTHER PUBLICATIONS

International Search Report dated Sep. 8, 2015 from International Application No. PCT/ES2015/070543, 5 pages.
(Continued)

*Primary Examiner* — Steven B McAllister
*Assistant Examiner* — Benjamin W Johnson
(74) *Attorney, Agent, or Firm* — Ohlandt, Greeley, Ruggiero & Perle, L.L.P.

(57) ABSTRACT

A volatile substance evaporator device comprising a heat source and a refill including said volatile substances, wherein the heat source is a flame that heats a transmission element which heats said refill for evaporating the volatile substances.

The result thereof is that the volatile substances evaporate properly without the need to use batteries or a similar power source, simply by the use of a flame, for example in the form of a candle, the financial cost thereof being very low.

13 Claims, 1 Drawing Sheet

(58) Field of Classification Search
USPC .......................................................... 122/4 R
See application file for complete search history.

(56) References Cited

U.S. PATENT DOCUMENTS

| | | | | |
|---|---|---|---|---|
| 6,482,365 | B1* | 11/2002 | Soller | ............... A01M 1/2066 |
| | | | | 422/125 |
| 6,503,459 | B1* | 1/2003 | Leonard | ............ A01M 1/2088 |
| | | | | 422/120 |
| 8,920,734 | B2* | 12/2014 | Furner | .................. A61L 9/037 |
| | | | | 422/125 |
| 2002/0031739 | A1* | 3/2002 | Papai | ..................... F21V 35/00 |
| | | | | 431/291 |
| 2005/0175513 | A1 | 8/2005 | Hart et al. | |
| 2008/0023568 | A1* | 1/2008 | Weggelaar | .............. A61L 9/12 |
| | | | | 239/43 |
| 2014/0010715 | A1* | 1/2014 | Furner | .................. A61L 9/037 |
| | | | | 422/125 |

FOREIGN PATENT DOCUMENTS

| | | |
|---|---|---|
| JP | 2004-89337 A | 3/2004 |
| WO | WO 01/19418 A1 * | 3/2001 |
| WO | 2012/044659 A1 | 4/2012 |

OTHER PUBLICATIONS

Written Opinion dated Sep. 8, 2015 from International Application No. PCT/E52015/070543, 7 pages.
European search report and opinion for the corresponding application EP15818861.5, dated Mar. 14, 2018, 7 pages.

* cited by examiner

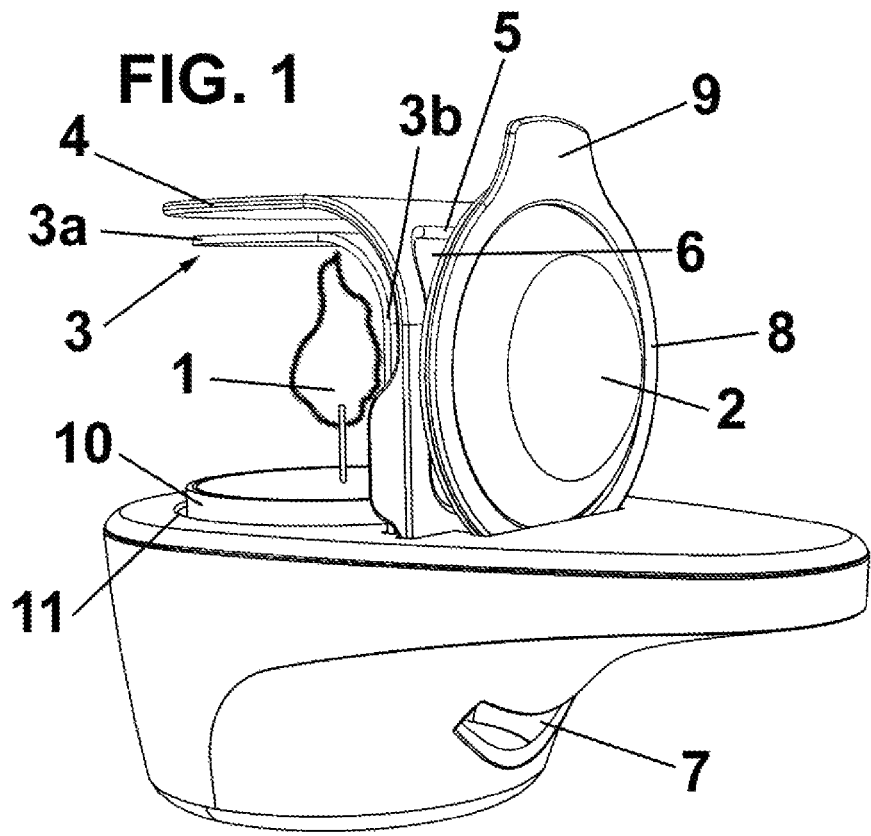
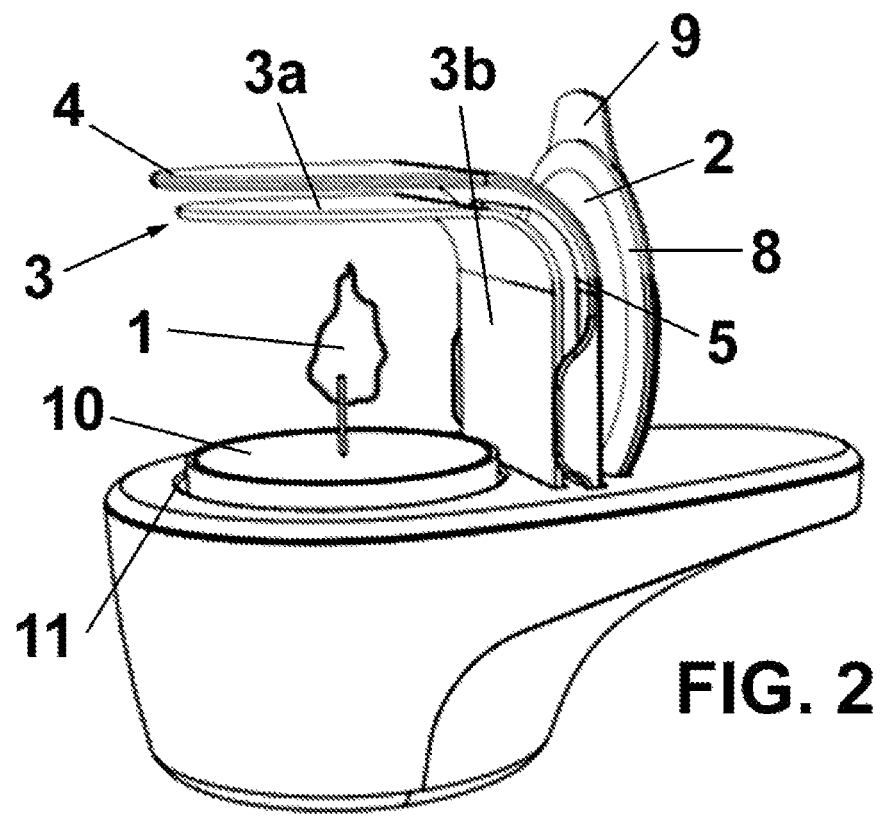

VOLATILE SUBSTANCE-EVAPORATOR DEVICE

The present invention relates to a volatile substance evaporator device comprising a heat emitter evaporating volatile substances contained in a refill.

BACKGROUND OF THE INVENTION

Conventional volatile substance evaporator devices comprise a heat emitter, for example, an electrical resistance, that heats a refill, for example, an impregnated tablet or a container. Furthermore, they also sometimes require the use of fans or other electromechanical elements to force the airflow for proper volatile substance diffusion.

The presence of electrical resistances, fans and other electromechanical elements for evaporating and diffusing volatile substances require the device to include power supply means.

The main drawback of conventional volatile substance evaporator devices is that they usually use replaceable batteries as said power supply means, from which they obtain the energy required for operation.

Batteries are not well accepted by consumers due to their financial impact, their dependency, and the added ecological impact entailed by using same.

There is therefore an obvious need for an evaporator device that does not require the use of batteries, allowing the use of an economical and eco-friendly power source.

DESCRIPTION OF THE INVENTION

The evaporator device of the invention solves the mentioned drawbacks, having other advantages that will be described below.

The volatile substance evaporator device according to the present invention comprises a heat source evaporating volatile substances of a refill.

The volatile substance evaporator device according to the present invention comprises a heat source and a refill including said volatile substances, and it is characterized in that said heat source is a flame that heats a transmission element which heats said refill for evaporating the volatile substances.

According to a preferred embodiment, said transmission element is a plate made of a heat transmitting material, and said plate preferably comprises a first portion to be heated by said flame and a second portion to heat said refill.

According to the preferred embodiment, said first portion and said second portion are substantially perpendicular to one another, and said second portion is preferably wider than said first portion.

Furthermore, said heat transmitting material is metal or ceramic, for example, aluminum, steel or copper.

Advantageously, the volatile substance evaporator device according to the present invention comprises a casing externally covering said transmission element, said casing comprising a hole in the area between the transmission element and the refill.

To prevent a user of the device from getting burned, said hole is covered by means of a protective grille.

The volatile substance evaporator device according to the present invention also advantageously comprises a convection groove to cause an airflow consisting of volatile substances.

Advantageously, said refill comprises an outer ring provided with a projection, which are made of a thermally insulating material, which allows removing the refill easily without the risk of a user getting burned.

According to a preferred embodiment, said refill is a thermoformed container with a membrane.

The volatile substance evaporator device according to the present invention results in volatile substances evaporating properly without having to use batteries or a similar power source, simply using a flame, for example in the form of a candle, the financial cost thereof being very low.

BRIEF DESCRIPTION OF THE DRAWINGS

To better understand what has been set forth, drawings schematically depicting a practical embodiment only by way of a non-limiting example are attached.

FIG. 1 is a front perspective view of the volatile substance evaporator device according to the present invention; and FIG. 2 is a rear perspective view of the volatile substance evaporator device according to the present invention.

DESCRIPTION OF A PREFERRED EMBODIMENT

The evaporator device according to the present invention comprises a heat source 1, such as a flame of a candle 10 provided with a wick, acting on a refill 2 including the volatile substances to be evaporated.

Said candle 10 is placed inside a housing 11 and can be replaced with a new candle as many times needed.

The evaporator device also comprises a transmission element 3 transmitting heat from the flame 1 to the refill 2, such that said heat will cause the volatile substances from the refill 2 to evaporate.

According to the embodiment depicted in the drawings, this transmission element 3 is a plate made of a heat transmitting material, for example metal or ceramic, such as aluminum, steel or copper, and defines a first portion 3a placed in the proximity of said flame 1 and a second portion 3b placed next to or in contact with said refill 2.

For example, the first portion 3a is placed at a distance between 0 and 100 mm with respect to the flame 1 and the second portion 3b is placed at a distance between 0 and 15 mm from the refill 2.

It is calculated that the first portion 3a can reach a temperature between 100° C. and 150° C., whereas the second portion 3b can reach a temperature between 70° C. and 90° C.

According to the depicted embodiment, said portions 3a and 3b of the transmission element 3 are substantially perpendicular to one another, as can be seen in the drawings, and said first portion 3a is narrower than said second portion 3b. In this manner, according to the depicted embodiment the first portion 3a is substantially horizontal and the second portion 3b is substantially vertical in the normal position of use of the evaporating device.

To make it easier for the transmission element 3 to maintain a high temperature and in order to protect the user, the evaporating device also comprises a casing 4 placed on the outer part of said transmission element 3, as can be seen in the drawings.

To allow the transmission element 3 to heat the refill 2, said casing 4 comprises a hole 5 in the area between the transmission element 3 and the refill 2. To prevent a user from directly contacting the transmission element 3 in this area, said hole 5 is covered with a grille 6, such that the temperature of the grille will be between 35° and 80° C.

The evaporating device according to the present invention also preferably comprises a convection groove 7 to cause an airflow consisting of volatile substances.

The refill 2 is in turn preferably a thermoformed container provided with a membrane to make it easier to evaporate the volatile substances, and comprises an outer ring 8 provided with a projection 9. This projection 9 allows the user to remove the refill 2 easily without any risk of getting burned, since the ring 8 and the projection 9 are made of a temperature-resistant material.

It is very simple to put the evaporating device according to the present invention in operation since it simply requires placing a candle 10 in its housing 11 and lighting it. The heat generated by the flame 1 of said candle 10 will be transmitted to the refill 2 previously placed in position through the transmission element 3, the heat of which will cause the volatile substances to evaporate without the need for electrical power supply means, such as batteries or the like. When the candle 10 has burned out, it must simply be replaced with a new one.

Although reference has been made to a specific embodiment of the invention, it is obvious for a person skilled in the art that the evaporator device described is susceptible to a number of variations and modifications, and that all the mentioned details can be replaced with other technically equivalent details without departing from the scope of protection defined by the attached claims.

The invention claimed is:

1. A volatile substance evaporator device comprising:
   a heat source and a refill including volatile substances, wherein said heat source is a flame that heats a transmission element which heats said refill for evaporating the volatile substances;
   wherein said transmission element further comprises a first portion to be heated by said flame and a second portion to heat said refill;
   wherein said first portion and said second portion are substantially perpendicular to one another; and
   a casing externally covering said transmission element,
   wherein said casing is disposed between said transmission element and said refill;
   wherein said casing comprises a hole in an area between said transmission element and said refill, said hole being adjacent said transmission element on a first side and adjacent said refill on a second side that is opposite the first side; and
   wherein a portion of said casing extends over the first portion of the transmission element and the heat source.

2. The volatile substance evaporator device according to claim 1, wherein said transmission element is a plate made of a heat transmitting material.

3. The volatile substance evaporator device according to claim 1, wherein said second portion is wider than said first portion.

4. The volatile substance evaporator device according to claim 2, wherein said heat transmitting material is metal or ceramic.

5. The volatile substance evaporator device according to claim 2, wherein said heat transmitting material is aluminum, steel or copper.

6. The volatile substance evaporator device according to claim 1, wherein said hole is covered by means of a protective grille.

7. The volatile substance evaporator device according to claim 1, comprising a convection groove to cause an airflow.

8. The volatile substance evaporator device according to claim 1, wherein said refill comprises an outer ring provided with a projection.

9. The volatile substance evaporator device according to claim 8, wherein said outer ring and said projection are made of a thermally insulating material.

10. The volatile substance evaporator device according to claim 1, wherein said refill is a thermoformed container with a membrane.

11. The volatile substance evaporator of claim 1, wherein said refill is not in contact with said casing.

12. The volatile substance evaporator of claim 1, wherein said refill is disposed separately from said casing.

13. A volatile substance evaporator device comprising:
    a heat source and a refill including volatile substances, wherein said heat source is a flame that heats a transmission element which heats said refill for evaporating the volatile substances;
    wherein said transmission element further comprises a first portion to be heated by said flame and a second portion to heat said refill;
    wherein said first portion and said second portion are substantially perpendicular to one another;
    a casing externally covering said transmission element,
    wherein said casing is disposed between said transmission element and said refill;
    wherein said casing comprises a hole in an area between said transmission element and said refill, said hole being adjacent said transmission element on a first side and adjacent said refill on a second side that is opposite the first side;
    wherein said casing further comprises a first portion and a second portion, that are substantially perpendicular to one another, and wherein the second portion of said casing is disposed between said transmission element and said refill; and
    wherein said first portion of said casing externally covers said first portion of said transmission element and said second portion of said casing externally covers said second portion of said transmission element.

\* \* \* \* \*